United States Patent [19]

Schulz et al.

[11] 4,263,453

[45] Apr. 21, 1981

[54] PROCESS FOR CONVERTING CYCLOHEXANE TO ADIPIC ACID

[75] Inventors: Johann G. D. Schulz, Pittsburgh; Anatoli Onopchenko, Monroeville, both of Pa.

[73] Assignee: Gulf Research & Development Company, Pittsburgh, Pa.

[21] Appl. No.: 101,621

[22] Filed: Dec. 10, 1979

[51] Int. Cl.$^3$ .................. C07C 51/31; C07C 55/14
[52] U.S. Cl. .................... 562/543; 562/593
[58] Field of Search .......................... 562/543

[56] References Cited

U.S. PATENT DOCUMENTS 4,158,739  6/1979  Schulz et al. .................. 562/543

Primary Examiner—Vivian Garner

[57] ABSTRACT

A process for converting cyclohexane to adipic acid which involves oxidizing cyclohexane with molecular oxygen in the presence of critical amounts of cobaltic ions and selected amounts of added water in an aliphatic monobasic acid while maintaining critical temperature and pressure in the reaction zone.

10 Claims, No Drawings

PROCESS FOR CONVERTING CYCLOHEXANE TO ADIPIC ACID

BACKGROUND OF THE INVENTION

1. Field of the Invention

This invention relates to a process for converting cyclohexane to adipic acid which comprises oxidizing cyclohexane with molecular oxygen in the presence of critical amounts of cobaltic ions and selected amounts of added water in an aliphatic monobasic acid while maintaining critical temperature and pressure in the reaction zone.

2. Description of the Prior Art

In our U.S. Pat. No. 4,032,569 we have disclosed a process for converting cyclohexane to adipic acid which comprises oxidizing cyclohexane with molecular oxygen in the presence of critical amounts of cobaltic ions in an aliphatic monobasic acid solvent while maintaining critical temperature pressure and contact time in the reaction zone.

In our U.S. Pat. No. 4,158,739 we have disclosed a process for converting cyclopentane to glutaric acid which comprises oxidizing cyclopentane with molecular oxygen in the presence of critical amounts of cobaltic ions in an aliphatic monobasic acid solvent while maintaining critical temperature, pressure and contact time in the reaction zone.

SUMMARY OF THE INVENTION

We have found that in our process defined in our U.S. Pat. No. 4,032,569, wherein we convert cyclohexane to adipic acid by oxidizing cyclohexane with molecular oxygen in the presence of critical amounts of cobaltic ions in an aliphatic monobasic acid while maintaining critical temperature and pressure in the reaction zone, higher yields of adipic acid are obtained by carrying out the reaction in the presence of selected amounts of added water.

The components required in the reaction zone are cyclohexane, an aliphatic monobasic acid solvent, cobaltic ions, molecular oxygen and added water.

The solvent used herein can be any aliphatic monobasic acid containing only primary and secondary hydrogen atoms in its structure and having from two to eight carbon atoms, preferably having from two to four carbon atoms. Examples of satisfactory monobasic acid solvents for this reaction include acetic, propionic, normal butyric, caprylic, pelargonic, trimethylacetic, normal caproic acid, etc. Of these we prefer to use acetic acid. The molar ratios of solvent to cyclohexane lie between about 1.5:1 to about 10:1 or even higher, but preferably between about 3:1 to about 9:1.

Cobalt must be present in the form of its cobaltic ion. The source from which the cobaltic ion is obtained is immaterial, as long as cobaltic ions are maintained in the reaction mixture during the reaction period. Thus, as a source therefor any cobaltous or cobaltic salt of an organic acid can be employed, such as cobaltous or cobaltic acetate, propionate, naphthenate, etc. Of these we prefer to use the cobalt acetate salts. In order to assist in obtaining the high conversions herein, the amount of cobalt present in the reaction mixture is critical and must be in excess of about 25 millimols of cobalt per mol of cyclohexane, preferably in the range of about 50 to about 100 millimols of cobalt per mol of cyclohexane. Cobalt in amounts up to about 150 millimols per mol of cyclohexane can be used, but amounts in excess thereof do not significantly improve the results.

In the oxidation of cyclohexane with molecular oxygen there is a period of induction before the reaction begins to proceed. This period of induction is believed to occur in order to oxidize the cobaltous ion to the active cobaltic ion and to promote the production of free radicals from the cyclohexane charge. This induction period can vary, for example, from about one half to as high as three hours, or even more. The induction period can be reduced, however, by the addition of an initiator to the reaction mixture. We believe the function of the initiator is to form free radicals faster than cyclohexane and to act as an oxidant to convert the cobaltous ions into the active cobaltic ions. The initiator can be any compound in which oxygen has a valence of minus one or compounds which on reacting with molecular oxygen will form compounds which contain oxygen having a valence of minus one. Such compounds include, for example, ozone; inorganic peroxides, such as sodium or hydrogen peroxide; organic peroxides, such as benzoyl peroxides; peracids, such as peracetic acid; aldehydes, such as acetaldehyde; ketones, such as methyl ethyl ketone and cyclohexanone; and ethers, such as dimethyl ether. We prefer to employ cyclic hydroperoxides or cyclic ketones corresponding in carbon structure to the cyclic hydroperoxides and cyclic ketones produced in the reaction. The amount of initiator can vary between about 0.1 to about 20 weight percent based on the cyclohexane, with preferred amounts of initiator being between about 0.3 to about three weight percent based on the cyclohexane.

Free molecular oxygen must also be present in the reaction zone. Thus, either air or oxygen itself can be employed. Another critical requirement herein in obtaining high conversions of cyclohexane to adipic acid is the partial pressure of oxygen over the reaction mixture. Accordingly, the partial pressure must be at least about 150 pounds per square inch absolute (about 10.8 kilograms per square centimeter) and can be as high as about 1000 pounds per square inch absolute, or even higher (about 70.5 kilograms per square centimeter), but excellent conversions are obtained when the oxygen pressure is in the range of about 200 to about 600 pounds per square inch absolute (about 24.6 to about 42 kilograms per square centimeter). Such pressures, moreover, are sufficient to maintain the reactants in the liquid phase.

As pointed out above, in order to increase the yields of adipic acid in the process defined and claimed in our U.S. Pat. No. 4,032,569, we must carry out the process in the presence of selected amounts of added free water. While the addition of even very small amounts of water to the reaction zone at the beginning of the process will be sufficient to obtain an increase in yield of adipic acid, we generally add at least about 0.5 weight percent of water, relative to the weight of the aliphatic monobasic acid solvent, but generally no more than about 15 weight percent of water, relative to the solvent, but preferably at least about 1.0 weight percent of water but usually no more than about 10 weight percent of water, relative to the solvent.

The reaction temperature is also critical and must be maintained in the range of about 85° to about 135° C., preferably in the range of about 90° to about 100° C. Thus, when temperatures in excess of the defined temperature ranges are employed there is an increasing tendency toward degradation of the desired adipic acid to glutaric and succinic acids. The reaction tends to go at an exceeding slow rate below the defined temperature ranges and would therefore be commercially unattractive.

In the process defined and claimed in our U.S. Pat. No. 4,032,569 we found that the reaction time was critical and could not be permitted to be in excess of about three hours. Above three hours only small amounts of additional conversion of cyclohexane was found and this was accompanied by the tendency of adipic acid to degrade to glutaric and succinic acid. In the present process, because of the presence of added water, reaction time is not critical and no appreciable degradation of adipic acid to glutaric or succinic acid occurs. Accordingly, we can permit the reaction to continue until oxygen absorption ceases. In this way the reaction can continue until no more cyclohexane can be converted. Of course, if desired the reaction can be terminated at any selected time short of the time when oxygen absorption ceases. Thus, the reaction time can be as low as about 0.5 hours, for example, but usually conversion of cyclohexane, or absorption of oxygen, will cease when about 12 hours have elapsed. In general, the reaction time will be at least about one hour but no more than about four hours. The reaction times will obviously be in addition to the induction periods.

The reaction mixture is preferably well agitated to insure better contacting of the reactants. Agitation can be provided by mechanical stirring devices aided by the ebullition caused by the introduction of the oxygen-containing gas below the surface of the liquid reaction mixture.

At the end of the reaction period the reaction mixture can be separated into its component parts by any convenient means. Thus, the contents of the reaction zone are cooled to room temperature, depressured and the reaction mixture withdrawn from the reaction zone. The reaction mixture is diluted with an equal volume of water and then heated on a steam bath to a temperature of about 100° C. for about one-half hour, or until the solution is pink, indicating the presence of cobaltous ions, and then evaporated to dryness. The residue is extracted with acetone to separate the organic products from the catalyst. The organic products will contain the desired adipic acid and smaller amounts of glutaric and succinic acids. The individual acids can be separated from each other in any conventional manner, for example, by crystallization from conventional solvents such as benzene or water. The catalyst will, at least in part, be present as the cobalt salt or adipic, glutaric and succinic acids. To recover these acids from the catalyst, the catalyst is treated with sodium hydroxide to release the chemically-bound acids from the catalyst, at the same time converting the cobalt salt to its hydroxide or oxide state. Filtration will result in a solution containing the acids as their sodium salts. The latter are sprung with hydrochloric acid to form the desired free acids. Recovery of these acids is effected by evaporating the solution to dryness and then extracting the residue with acetone to separate the acids from sodium chloride. Evaporation of acetone will leave behind the additional adipic, glutaric and succinic acids. The catalyst can also be treated with concentrated hydrochloric acid and on evaporation to dryness will result in the formation of free organic acids and inorganic salts. These can readily be separated by extraction with a solvent, such as acetone mentioned above. In a continuous oxidation procedure, the amount of product acids tied up with the cobalt will reach a steady-state concentration, and for practical reasons can be ignored in calculations as the catalyst is returned for recycle.

DESCRIPTION OF PREFERRED EMBODIMENTS

EXAMPLE I

A series of runs was carried out in which all of the components of a reaction mixture, except molecular oxygen, were added to a 1-liter, stirred, 316-stainless steel autoclave. The contents of the autoclave were heated to desired temperature and pressured with molecular oxygen to desired pressure. Time between the moment when the reaction mixture is brought to the defined temperature and pressure levels and when oxygen absorption begins (indicating the start of oxidation) is defined as the induction period. Each run was terminated when oxygen absorption ceased. The time between the start of oxygen absorption and when the reaction mixture is withdrawn from the reaction conditions is defined as reaction time. The products obtained were then subjected to recovery procedures as defined above. The data obtained are set forth below in Table I. Conversion was calculated by dividing the weight of the cyclohexane reacted by the weight of the cyclohexane charged times one hundred. Efficiency was based on the percent of cyclohexane reacted that was converted to the indicated compound.

TABLE I

| Run No. | 1 | 2 | 3 | 4 |
|---|---|---|---|---|
| Charge | | | | |
| Cobaltous Acetate Tetrahydrate, Grams (Millimols Per Mol of Cyclohexane) | 20 (95) | 20 (95) | 20 (95) | 20 (95) |
| Cyclohexane, Grams | 70 | 70 | 70 | 70 |
| Methyl Ethyl Ketone, Grams | 15 | 15 | 15 | 15 |
| Acetic Acid, Grams | 420 | 420 | 420 | 420 |
| Water Added at Beginning of Reaction, Grams (Weight Percent Based on Acetic Acid) | None | 15 (3.6) | 30 (7.2) | 45 (10.7) |
| Reaction Conditions | | | | |
| Temperature, °C. | 95 | 95 | 95 | 95 |
| Partial Pressure of Oxygen, Pounds Per Square Inch Absolute (Kilograms per Square Centimeter) | 300 (20.4) | 300 (20.4) | 300 (20.4) | 300 (20.4) |
| Induction Time, Hours | 1.3 | 3.5 | 3.0 | 4.3 |
| Reaction Time, Hours | 2 | 2.5 | 2.5 | 2.0 |
| Product Data | | | | |
| Solids Recovered, Grams | 104 | 108 | 110 | 102 |
| Conversion, Percent | 90 | 92 | 94 | 86 |
| Percent Molar Selectivity To | | | | |

TABLE I-continued

| Run No. | 1 | 2 | 3 | 4 |
|---|---|---|---|---|
| Adipic Acid | 70.7 | 76.7 | 80.6 | 80.5 |
| Glutaric Acid | 14.7 | 11.6 | 9.3 | 10.6 |
| Succinic Acid | 13.9 | 11.7 | 9.8 | 9.4 |
| Yield of Adipic Acid | 63.6 | 70.6 | 75.8 | 69.2 |
| Percent Increase In Yield of Adipic Acid Because of Added Water | Base Run | +11 | +19 | +9 |

A study of the data in FIG. I clearly illustrates the improvement herein. In each of Runs Nos. 2, 3 and 4, wherein free water was initially added to the reaction mixture, there was a significant increase in yields of adipic acid over Run No. 1 wherein no additional free water was added to the reaction mixture. These data also illustrate the effect of water on increased selectivity to adipic acid as the amount of water is increased. These results are both unusual and unexpected. Since the oxidation of cyclohexane is accompanied by the formation of water, it is most unusual that the addition of a small amount of water initially would beneficially influence the yields of adipic acid. In addition in each of the runs the cobalt salt was introduced in the form of cobaltous acetate tetrahydrate. It is apparent from the above data that whatever additional water is introduced into the system by way of the cobalt salt that the addition of selected amounts of free water at the beginning of the operation is required to increase the yields of adipic acid.

We have additionally been surprised that the process defined and claimed herein is specific to the conversion of cyclohexane to adipic acid. In our two patents referred to above, namely, U.S. Pat. Nos. 4,032,569 and 4,158,739, we found the conditions necessary to convert cyclohexane and cyclopentane, respectively, to adipic acid and glutaric acid, respectively, to be somewhat similar. Having found that we were able to increase the yield of adipic acid in the process of U.S. Pat. No. 4,032,569 by carrying out the reaction in the presence of added water, we were of the opinion that similar improvements would be obtained in obtaining increased yields of glutaric acid in the process of U.S. Pat. No. 4,158,739 also by adding water to the reaction mixture. We found, instead, that while the improvement was obtained in the process of U.S. Pat. No. 4,032,569, no appreciable improvement was obtained by adding water to the reaction system of U.S. Pat. No. 4,158,739. This is shown in Example II below.

EXAMPLE II

An additional series of runs was carried out, following the procedure of Example I, except that cyclopentane was subjected to oxidation in place of cyclohexane. The results are summarized below in Table II.

TABLE II

| Run No. | 5 | 6 | 7 |
|---|---|---|---|
| Charge | | | |
| Cobaltous Acetate Tetrahydrate, Grams (Millimols Per Mol of Cyclopentane) | 20 (97) | 20 (97) | 20 (97) |
| Cyclopentane, Grams | 58 | 58 | 58 |
| Methyl Ethyl Ketone, Grams | 10 | 10 | 10 |
| Acetic Acid, Grams | 400 | 400 | 400 |
| Water Added At Beginning of Reaction, Grams (Weight Percent Based on Acetic Acid) | None | 10 (2.5) | 25 (6.3) |
| Reaction Conditions | | | |
| Temperature, °C. | 100 | 110 | 110 |
| Partial Pressure of Oxygen, Pounds Per Square Inch Absolute (Kilograms Per Square Centimeter) | 300 (20.4) | 300 (20.4) | 300 (20.4) |
| Induction Time, Minutes | 69 | 38 | 58 |
| Reaction Time, Hours | 1.4 | 2.3 | 2.5 |
| Product Data | | | |
| Solids Recovered, Grams | 113 | 91 | 86 |
| Conversion, Percent | 87 | 85 | 80 |
| Percent Molar Selectivity To | | | |
| Glutaric Acid | 81 | 79 | 80 |
| Succinic Acid | 19 | 21 | 20 |
| Yield of Glutaric Acid | 70.5 | 67.2 | 64 |
| Decrease In Yield of Glutaric Acid Because of Added Water | Base Run | −4.7 | −9.2 |

It will be seen from Table II that, unlike cyclohexane, when a selected amount of water is added to the reaction mixture in the process of our U.S. Pat. No. 4,158,739, wherein cyclopentane is converted to glutaric acid, decreased yields of glutaric acid are obtained. For practical purposes, therefore, addition of water had essentially little effect on glutaric acid selectivity but had an adverse effect on the cyclopentane conversion level in contrast to the results obtained with cyclohexane.

Obviously, many modifications and variations of the invention, as hereinabove set forth, can be made without departing from the spirit and scope thereof, and therefore only such limitations should be imposed as are indicated in the appended claims.

We claim:

1. In a process wherein cyclohexane is converted to adipic acid in a system consisting essentially of cyclcohexane, an aliphatic monobasic acid solvent, cobaltic ions and molecular oxygen, wherein the cyclohexane is subjected to oxidation with oxygen in the presence of cobaltic ions in an aliphatic monobasic acid having only primary and secondary hydrogen atoms and from two to eight carbon atoms, the amount of cobalt present being in excess of about 25 millimols of cobalt per mol of cyclohexane, while maintaining a temperature of about 85° to about 135° C. and an oxygen partial pressure of at least about 150 pounds per square inch absolute, improving the yield of adipic acid by adding free water to the reaction system, the amount of water added being in the range of about 0.5 to about 15 weight percent based on the weight of aliphatic monobasic acid solvent.

2. The process of claim 1 wherein the amount of water added is in the range of about 1.0 to about 10 weight percent based on the weight of the aliphatic monobasic acid solvent.

3. The process of claim 1 wherein up to about 150 millimols of cobalt are present per mol of cyclohexane.

4. The process of claim 1 wherein about 50 to about 100 millimols of cobalt are present per mol of cyclohexane.

5. The process of claim 1 wherein the temperature is in the range of about 90° to about 100° C.

6. The process of claim 1 wherein the oxygen partial pressure is in the range of about 200 to about 600 pounds per square inch absolute.

7. The process of claim 1 wherein the aliphatic monobasic acid has from two to four carbon atoms.

8. The process of claim 1 wherein the aliphatic monobasic acid is acetic acid.

9. The process of claim 1 wherein the molar ratio of aliphatic monobasic acid to cyclohexane is about 1.5:1 to about 10:1.

10. The process of claim 1 wherein the molar ratio of aliphatic monobasic acid to cyclohexane is about 3:1 to about 9:1.

* * * * *